(12) United States Patent
Cho et al.

(10) Patent No.: US 8,362,263 B2
(45) Date of Patent: Jan. 29, 2013

(54) CRYSTALLINE S-(−)-AMLODIPINE ADIPIC ACID SALT ANHYDROUS AND PREPARATION METHOD THEREOF

(75) Inventors: Il Hwan Cho, Seoul (KR); Yong Sik Youn, Gyeonggi-do (KR); Seog Beom Song, Gyeonggi-do (KR); Dong Kwon Lim, Gyeonggi-do (KR)

(73) Assignee: CJ Cheiljedang Corporation (KR)

(*) Notice: Subject to any disclaimer, the term of this patent is extended or adjusted under 35 U.S.C. 154(b) by 696 days.

(21) Appl. No.: 12/447,530

(22) PCT Filed: Oct. 26, 2007

(86) PCT No.: PCT/KR2007/005335
§ 371 (c)(1),
(2), (4) Date: Apr. 28, 2009

(87) PCT Pub. No.: WO2008/054096
PCT Pub. Date: May 8, 2008

(65) Prior Publication Data
US 2010/0069642 A1    Mar. 18, 2010

(30) Foreign Application Priority Data

Oct. 31, 2006 (KR) .......... 10-2006-0106185

(51) Int. Cl.
*A61K 31/44* (2006.01)
*C07D 213/803* (2006.01)
(52) U.S. Cl. .................................. 546/321; 514/356
(58) Field of Classification Search .......................... None
See application file for complete search history.

(56) References Cited

U.S. PATENT DOCUMENTS

| | | | |
|---|---|---|---|
| 5,750,707 A * | 5/1998 | Spargo | 546/321 |
| 6,046,338 A | 4/2000 | Spargo | |
| 6,057,344 A | 5/2000 | Young | |
| 6,080,761 A | 6/2000 | Chahwala et al. | |
| 6,291,490 B1 | 9/2001 | Young | |
| 7,015,238 B2 * | 3/2006 | Lim et al. | 514/356 |
| 2004/0058967 A1 * | 3/2004 | Lim et al. | 514/355 |

FOREIGN PATENT DOCUMENTS

| | | |
|---|---|---|
| CN | 1343663 A | 4/2002 |
| EP | 0089167 A2 | 9/1983 |
| KR | 20040023474 A | 3/2004 |
| KR | 20040025549 A | 3/2004 |
| KR | 20050037498 A | 4/2005 |
| WO | 02079158 A1 | 10/2002 |
| WO | 03043989 A1 | 5/2003 |
| WO | 2004/024690 A1 | 3/2004 |
| WO | 2004026834 A1 | 4/2004 |
| WO | WO 2004/026834 A1 * | 4/2004 |
| WO | 2005/058825 A1 | 6/2005 |
| WO | 2005/089353 A2 | 9/2005 |
| WO | 2008/060093 A1 | 5/2008 |
| WO | 2008/069469 A1 | 6/2008 |
| WO | 2008/091085 A1 | 7/2008 |

OTHER PUBLICATIONS

Hillery, AM. et al. Drug Delivery and Targeting. Taylor & Francis. 2001, p. 146, last paragraph.*
Poole, JW. et al. Dissolution Behavior and Solubility of Anhydrous and Dihydrate Forms of Wy-4508, an Aminoalicyclic Penicillin. Journal of Pharmaceutical Sciences. 2006, vol. 59(9), p. 1267.*
International Search Report, PCT/KR2007/005335, dated Feb. 4, 2008.
Supplementary European Search Report, EP 07833643, dated Nov. 17, 2010.

* cited by examiner

*Primary Examiner* — Janet Andres
*Assistant Examiner* — Heidi Reese
(74) *Attorney, Agent, or Firm* — Lerner, David, Littenberg, Krumholz & Mentlik, LLP

(57) ABSTRACT

Disclosed are crystalline S-(−)-amlodipine adipic acid salt anhydrous and a preparation method thereof. The crystalline S-(−)-amlodipine adipic acid salt anhydrous exhibits excellent physical and chemical properties including non-hygroscopicity, solubility, thermal stability, and photostability, and is superior in formulation processability and long-term storage safety.

7 Claims, 1 Drawing Sheet

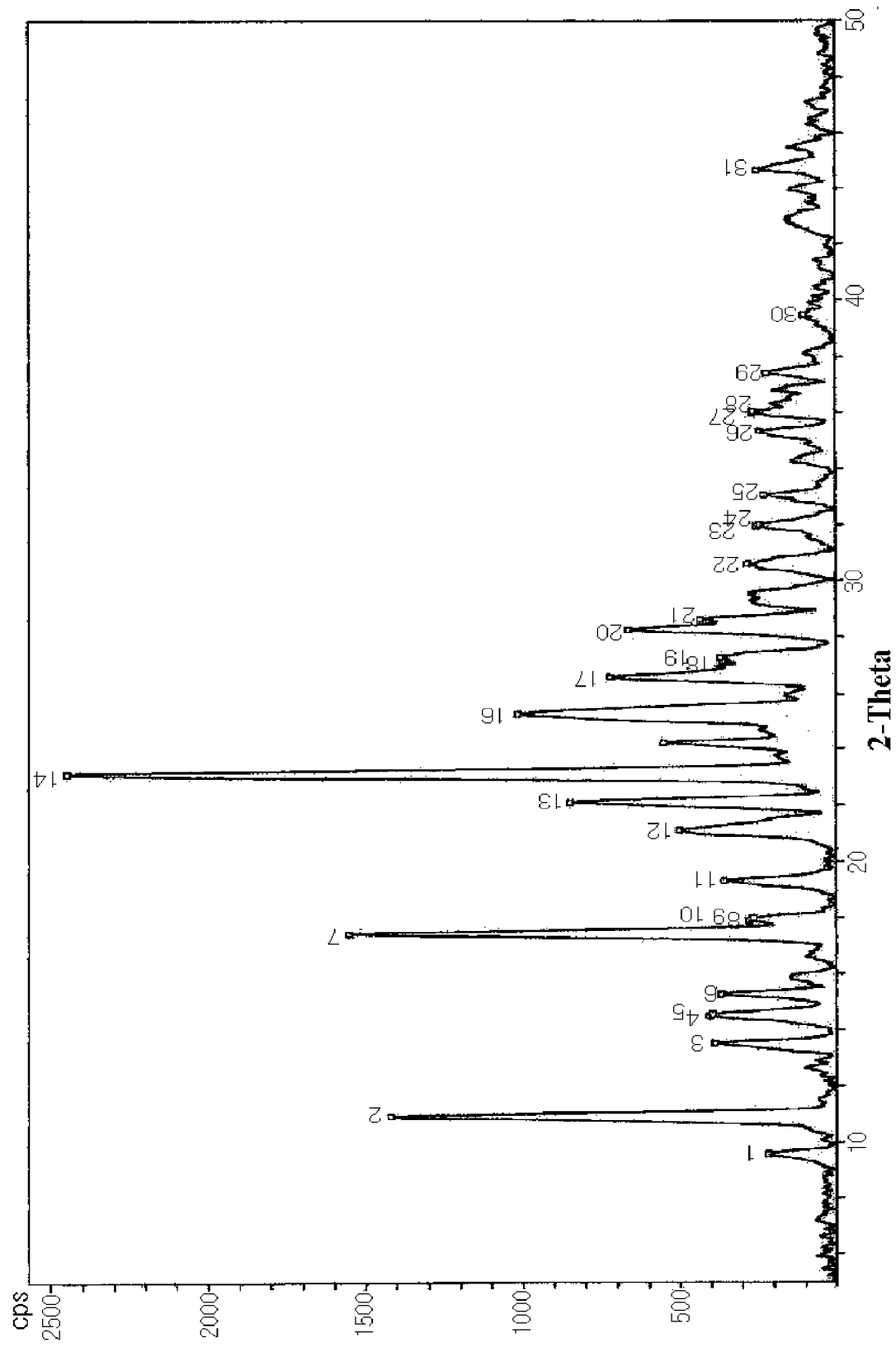

CRYSTALLINE S-(−)-AMLODIPINE ADIPIC ACID SALT ANHYDROUS AND PREPARATION METHOD THEREOF

TECHNICAL FIELD

The present invention relates to crystalline S-(−)-amlodipine adipic acid salt anhydrous and a method of preparing the same.

BACKGROUND ART

Amlodipine, the IUPAC Name of 3-ethyl-5-methyl-2-(2-aminoethoxymethyl)-4-(2-chlorophenyl)-1,4-dihydro-6-methyl-3,5-pyridinedicarboxylate, is a long-acting calcium channel blocker useful in the treatment of cardiovascular diseases, such as angina pectoris, hypertension, congestive heart failure, etc.

Amlodipine is a racemic compound with a chiral center. In general, pure stereoisomers are known to have better therapeutic effects than racemic mixtures. Furthermore, chiral compounds tend to have different pharmacokinetic profiles, depending on the steric arrangement of the isomer compounds or their salts. There are two possible stereoisomers of amlodipine, because of its one chiral center, that is, R-(+)-amlodipine and (S-(−)-amlodipine, that are different from each other in pharmacokinetic profile. The R(+) isomer of amlodipine is a potent inhibitor of smooth muscle cell migration despite its lack of calcium channel-blocking activity (U.S. Pat. No. 6,080,761). It is useful for preventing and treating atherosclerosis. On the other hand, the (S)-(−)-isomer of amlodipine is a potent calcium channel blocker. For ideal use as a calcium channel blocker, amlodipine is administered in the form of S-(−)-amlodipine, substantially free of its (+) stereoisomer (U.S. Pat. No. 6,057,344). U.S. Pat. No. 6,291,490 also discloses S-(−)-amlodipine, teaching that S-(−)-amlodipine avoids the adverse effect of amlodipine in racemic mixtures.

European Patent Publication No. 89,167 discloses an acid adduct as an example of a pharmaceutically acceptable amlodipine salt. The pharmaceutically acceptable acid adduct is formed from an acid that forms a nontoxic acid adduct including a pharmaceutically acceptable anion, such as hydrochloride, hydrobromide, sulfate, phosphate, acetate, malate, fumarate, lactate, tartrate, citrate or gluconate.

As distinct from salts of racemic amlodipine, almost none of which form hydrates, pharmaceutically acceptable salts of S-(−)-amlodipine are in the most part in the form of hydrates. Korean Patent Laid-Open Publication No. 10-2005-37498 describes hydrophilic S-(−)-amlodipine salts or hydrates thereof and pharmaceutical compositions comprising the same. Examples of the hydrates of S-(−)-amlodipine salts include S-(−)-amlodipine benzenesulfonatedihydrate, S-(−)-amlodipine acetate monohydrate, S-(−)-amlodipine aspartate dihydrate, S-(−)-amlodipine tartrate dihydrate, S-(−)-amlodipine sulfate dihydrate, and S-(−)-amlodipine hydrobromide monohydrate.

Korean Patent Laid-Open Publication No. 10-2004-23474 discloses crystalline S-(−)-amlodipine nicotinate dihydrate and a preparation method thereof.

For use in pharmaceutical formulations, S-(−)-amlodipine salts must meet physical and chemical standards: 1) non-hygroscopicity, 2) high solubility, 3) high thermal stability, 4) high photostability and 5) low viscosity. In addition, requirements of acids suitable for use in pharmaceutically acceptable salts include non-pharmaceutical properties, harmlessness, and processing feasibility.

Currently commercially available is S-(−)-amlodipine besylate, which is in the form of 2.5 hydrate (water content: 7.5%). The high water content requires precise water control and scrupulous care for the preparation and storage of S-(−)-amlodipine.

As such, salts in a hydrous form suffer from disadvantages in that they are difficult or inconvenient to manage because their hydration varies depending on processing conditions, are hygroscopic, and are inferior in thermal stability to those in anhydrous forms. When processed into pharmaceutical formulations, hydrous salts show high viscosity.

*Existing in the form of hydrates, most currently used S-(−)-amlodipine salts are difficult to formulate into pharmaceutical preparations.

Therefore, there is a need for pharmaceutical salts of S-(−)-amlodipine that are imparted with physical properties good enough to overcome the problems encountered in the prior art.

DISCLOSURE OF INVENTION

Technical Problem

Leading to the present invention, intensive and thorough research into S-(−)-amlodipine salts, conducted by the present inventors, aiming to solve the problems encountered with hydrous forms of optically pure isomers, resulted in the finding that an anhydrate of S-(−)-amlodipine adipate, produced by the reaction of S-(−)-amlodipine with adipic acid, exhibits excellent physical and chemical properties including non-hygroscopicity, solubility, thermal stability, and photostability, and is superior in formulation processability and long-term storage safety.

Technical Solution

It is an object of the present invention to provide crystalline S-(−)-amlodipine adipic acid salt anhydrous, and a method for preparing the same.

BRIEF DESCRIPTION OF THE DRAWINGS

FIG. 1 is an XRD diagram of crystalline S-(−)-amlodipine adipic acid salt anhydrous according to the present invention.

BEST MODE FOR CARRYING OUT THE INVENTION

In accordance with an aspect thereof, the present invention provides crystalline S-(−)-amlodipine adipic acid salt anhydrous, represented by the following Chemical Formula 1:

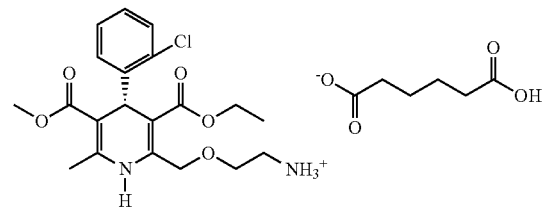

<Chemical Formula 1>

The crystalline S-(−)-amlodipine adipic acid salt anhydrous in accordance with the present invention has X-ray diffraction peaks at diffraction angles of 9.6°, 11.0°, 13.54°, 14.52°, 14.58°, 15.30°, 17.48°, 17.92°, 17.98°, 18.02°, 19.34°, 21.14°, 22.14°, 23.20°, 24.26°, 25.32°, 26.60°, 27.14°, 27.26°, 28.26°, 28.62°, 30.62°, 31.96°, 32.02°, 33.06°, 35.36°, 35.98°, 36.04°, 37.4°, and 44.68° and a melting point of 134~136° C.

Compared to commercially available S-(−)-amlodipine besylate 2.5 hydrate (brand name: Levotension), the crystalline S-(−)-amlodipine adipic acid salt anhydrous in accordance with the present invention has an equivalent or higher level of non-hygroscopicity and thermal stability, and exhibits 7 to 30 times higher solubility at pH 1.2~6.8. Particularly, being far superior in photostability and formulation processability, the crystalline S-(−)-amlodipine adipic acid salt anhydrous can be used as an anti-hypertensive that is required to be stored for a long period of time due to a prolonged term of use thereof. By the term "photostability" as used herein for the compound of the present invention, it is meant that after exposure to a light source at 25° C. for 4 weeks, the content of the active ingredient remains 90% or more, preferably 95% or more, and more preferably 98% or more of its activity.

Anhydrous as it is, the compound of the present invention is superior in solubility over S-(−)-amlodipine besylate 2.5 hydrate as well as anhydrates of racemic amlodipine adipate.

In accordance with another aspect thereof, the present invention provides a method for preparing an anhydrate of crystalline S-(−)-amlodipine adipate.

As illustrated by the following Reaction Scheme 1, the preparation method according to the present invention features a reaction between S-(−)-amlodipine and adipic acid in an inert solvent to afford crystalline S-(−)-amlodipine adipic acid salt anhydrous.

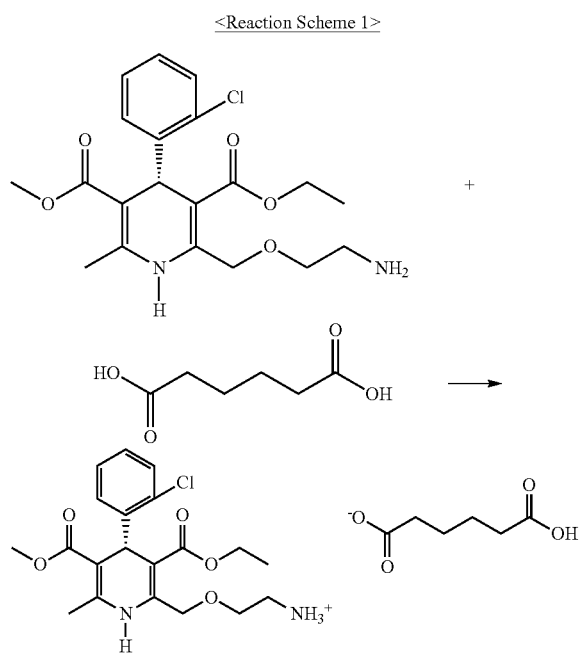

<Reaction Scheme 1>

Adipic acid, the material for the compound of the present invention, is currently used as a food additive and is a stable colorless powder that is neither hygroscopic nor caustic. In addition, adipic acid is sufficiently harmless to the body to be safe for use in pharmaceutical preparations and sufficiently convenient to handle to be applicable in the mass production of pharmaceutical preparations.

Examples of the inert solvent suitable for the preparation method of the present invention include ethyl acetate, ethanol, isopropanol, acetonitrile, hexane, and isopropyl ether, with preference for ethanol, isopropanol and a mixed solvent thereof, and higher preference for a mixed solvent of ethanol and isopropanol. In the mixed solvent of ethanol and isopropanol, ethanol may be used in an amount from 0 to 100%, with propanol correspondingly ranging from 0 to 100%. Preferably, the mixed solvent is composed of 33% ethanol and 67% isopropanol. When used in the preparation of S-(−)-amlodipine adipate, the mixed solvent of ethanol and isopropanol guarantees that the product is imparted with non-hygroscopicity and crystallinity. On the other hand, the use of distilled water ($H_2O$) as a solvent affords hygroscopic S-(−)-amlodipine adipate.

A detailed description is given of the preparation method of the present invention, below.

First, S-(−)-amlodipine is dissolved in an inert solvent. The inert solvent is used in a volumetric amount (ml) 10~100 times the weight (g) of the S-(−)-amlodipine used, and preferably in a volumetric amount (ml) 20~30 times the weight (g) of the S-(−)-amlodipine used. To this solvent is added adipic acid in an amount of 1~2 equivalents, and preferably 1.02~1.2 equivalents per equivalent of S-(−)-amlodipine. Reaction at −5~30° C., preferably at 15~25° C. for 0.5~5 hours, and preferably 1~3 hours, affords crystalline S-(−)-amlodipine adipic acid salt anhydrous.

Through the preparation method of the present invention, the crystalline S-(−)-amlodipine adipic acid salt anhydrous can be produced at a yield of 90% or higher.

The crystalline S-(−)-amlodipine adipic acid salt anhydrous produced by the method of the present invention exhibits excellent physical and chemical properties including non-hygroscopicity, solubility, thermal stability, photostability, formulation processability and long-term storage safety.

In accordance with a further aspect thereof, the present invention provides a pharmaceutical composition for the prevention or treatment of cardiovascular diseases, comprising as an active ingredient the crystalline S-(−)-amlodipine adipic acid salt anhydrous prepared by the method of the present invention.

In addition to the crystalline S-(−)-amlodipine adipic acid salt anhydrous, the pharmaceutical composition of the present invention may comprise at least one known active ingredient useful in the prevention or treatment of cardiovascular diseases.

For dosage forms, the pharmaceutical composition of the present invention may be formulated in combination with at least one pharmaceutically acceptable vehicle. Examples of the pharmaceutically acceptable vehicle include saline, sterile water, Ringer's solution, buffered saline, a dextrose solution, a maltodextrin solution, glycerol, ethanol and combinations thereof. If necessary, a conventional additive, such as an antioxidant, a buffer, an anti-bacterial agent, etc., may be added to the composition. Also, the pharmaceutical composition of the present invention may optionally be formulated with a diluent, a dispersing agent, a surfactant, a binder and/or a lubricant, into an injection, such as an aqueous solution, a suspension, an emulsion, etc., a tablet, a capsule, a granule or a pill. Furthermore, the formulation of the pharmaceutical composition of the present invention may be conducted according to methods known in the art, such as that described in Remington's Pharmaceutical Science (most recent edition), Mack Publishing Company, Easton Pa., depending on the disease and/or ingredients.

The pharmaceutical composition of the present invention may be administered orally or non-orally (e.g., intravenously, subcutaneously, intraperitoneally, or topically) at a dose depending on various factors including the patient's weight, age, gender, state of health, diet, administration route, number of administrations, excretion rate, severity of illness, and the like. The crystalline S-(−)-amlodipine adipic acid salt anhydrous may be administered in a single dose or in several doses per day with a daily dose ranging from 0.1 to 20 mg/kg, and preferably from 2.5 to 5.0 mg/kg.

For the prevention or treatment of cardiovascular diseases, the pharmaceutical composition of the present invention may be used alone or in combination with other therapies, including surgical therapy, hormonal therapy, and/or chemical therapy, or a biological response regulator.

A better understanding of the present invention may be obtained through the following examples, which are set forth to illustrate, but are not to be construed as the limit of the present invention.

MODE FOR THE INVENTION

EXAMPLE 1

Preparation of Non-Hygroscopic Crystalline S-(−)-Amlodipine Adipic

Acid Salt Anhydrous 13 g (0.0316 mol) of S-(−)-amlodipine was dissolved in a mixture of 173 ml of isopropanol and 87 ml of ethanol. To this solution was added 4.85 g (1.05 eq.) of adipic acid, followed by stirring at 25° C. for 2 hours to afford a precipitate. After filtration, the precipitate was washed and purified with 50 ml of isopropanol and ethanol (2:1) and dried in a vacuum to produce 15.5 g of an anhydrate of S-(−)-amlodipine adipate as a white crystalline solid (yield: 91%, water content: 0.15%).

The crystalline S-(−)-amlodipine adipic acid salt anhydrous was analyzed to determine diffraction angles using an X-ray powder diffraction method, and measured for melting point with an increase in temperature at a rate of 1° C./min from 50 to 200° C. through a melting point measurement method (Melting Point Method I of General Test Methods in Korean Pharmacopeia VIII or Melting Point-Capillary Method of European Pharmacopoeia IV).

The X-ray diffraction spectrum of the crystalline S-(−)-amlodipine adipic acid salt anhydrous according to the present invention is shown in FIG. 1, and its elemental analysis data and melting point are given as follows:

Diffraction Angles: 9.6°, 11.0°, 13.54°, 14.52°, 14.58°, 15.30°, 17.48°, 17.92°, 17.98°, 18.02°, 19.34°, 21.14°, 22.14°, 23.20°, 24.26°, 25.32°, 26.60°, 27.14°, 27.26°, 28.26°, 28.62°, 30.62°, 31.96°, 32.02°, 33.06°, 35.36°, 35.98°, 36.04°, 37.42°, 44.68°, Elemental Analysis for $C_{26}H_{35}ClN_2O_8$ [found (C: 56.32, H: 6.34, N: 5.08, O: 25.91), calculated (C: 56.26, H: 6.36, N: 5.05, O: 25.94)], m.p.: 134~136° C.

EXAMPLE 2

Preparation of Hygroscopic Crystalline S-(−)-Amlodipine Adipic

Acid Salt Anhydrous 13 g (0.0316 mol) of S-(−)-amlodipine was slurried with 120 ml of distilled water, followed by the addition of 5 g (1.05 eq.) of adipic acid thereto. Stirring for 5 hours formed a crystalline precipitate in the complete solution. After filtration, the crystalline precipitate was washed with 50 ml of distilled water and dried at 40° C. in a vacuum to afford 16 g of S-(−)-amlodipine (yield: 89%, water content: 0.7%).

The elemental analysis data and melting point of hygroscopic crystalline S-(−)-amlodipine adipic acid salt anhydrous are given as follows:

Elemental analysis for $C_{26}H_{35}ClN_2O_8$ [found (C: 56.32, H: 6.38, N: 5.04, O: 25.99), calculated (C: 56.26, H: 6.36, N: 5.05, O: 25.94)].

m.p.: 134~136° C.

COMPARATIVE EXAMPLE 1

Preparation of S-(−)-Amlodipine Besylate 2.5 Hydrate

S-(−)-amlodipine was prepared according to the method described in U.S. Pat. No. 6,046,338. S-(−)-amlodipine besylate 2.5 hydrate was prepared from S-(−)-amlodipine using the method disclosed in Korean Patent Laid-Open Publication No. 10-2005-37498.

COMPARATIVE EXAMPLE 2

Preparation of Crystalline Racemic Amlodipine Adipic

Acid Salt Anhydrous

The crystalline racemic amlodipine adipic acid salt anhydrous was prepared from racemic amlodipine using the method described in Korean Patent No. 10-0596369.

EXPERIMENTAL EXAMPLE 1

Hygroscopicity Test

The crystalline S-(−)-amlodipine adipic acid salt anhydrous prepared in Examples 1 and 2, the S-(−)-amlodipine besylate 2.5 hydrate prepared in Comparative Example 1, and the anhydrate of crystalline racemic amlodipine adipate prepared in Comparative Example 2 were measured for water content (K.F. moisture %) at 25° C. under various humidity conditions (25%, 60%, 75%, and 95%).

The results are summarized in Table 1, below.

TABLE 1

| | Storage Conditions (RH) | | | |
|---|---|---|---|---|
| | 25% | 60% | 75% | 95% |
| | | Storage Period | | |
| | Initial | Post 1 Week | Post 1 Week | Post 1 Week | Post 1 Week |
| Ex. 1 | 0.15% | 0.15% | 0.15% | 0.14% | 0.16% |
| Ex. 2 | 0.7% | 0.8% | 0.9% | 1.3% | 1.62% |
| C. Ex. 1 | 7.8% | 7.55% | 7.6% | 7.85% | 7.9% |
| C. Ex. 2 | 0.10% | 0.10% | 0.09% | 0.15% | 0.17% |

As shown in Table 1, the non-hygroscopic S-(−)-amlodipine adipic acid salt anhydrous prepared in Example 1 and the crystalline racemic amlodipine adipic acid salt anhydrous prepared in Comparative Example 2 were found to show no hygroscopicity under various humidity conditions. In contrast, the hygroscopic S-(−)-amlodipine adipic acid salt anhydrous prepared using distilled water in Example 2 increased in hygroscopicity to as high as 1.62% after 1 weeks at 95%

RH. S-(−)-amlodipine besylate 2.5 hydrate of Comparative Example 1, which is currently commercially available, was high in water content from the beginning.

EXPERIMENTAL 2

Solubility Test

The crystalline S-(−)-amlodipine adipic acid salt anhydrous prepared in Example 1, the S-(−)-amlodipine besylate 2.5 hydrate prepared in Comparative Example 1, and the crystalline racemic amlodipine adipic acid salt anhydrous prepared in Comparative Example 2 were measured for solubility at 25° C. under various pH conditions.

The results are summarized in Table 2, below.

TABLE 2

| Solvents | Ex. 1 | C. Ex. 1 | C. Ex. 2 | Note |
|---|---|---|---|---|
| Water | 18.59 | 2.51 | 1.53 | pH buffered solution according to Korean Pharmacopeia |
| pH 1.2 | 81.68 | 3.12 | 3.68 | |
| pH 4.0 | 57.05 | 2.94 | 2.27 | |
| pH 6.8 | 41.31 | 1.39 | 4.48 | |

(Unit: mg/ml)

As is understood from the data of Table 2, the solubility of the crystalline S-(−)-amlodipine adipic acid salt anhydrous of the present invention (Example 1) was about 7~30 times as high as that of S-(−)-amlodipine besylate 2.5 hydrate (Comparative Example 1) or the crystalline racemic amlodipine adipic acid salt anhydrous (Comparative Example 2) in distilled water and buffers over a wide range of pH values.

EXPERIMENTAL EXAMPLE 3

Thermal Stability Test

1. Thermal Stability in Solid State

The crystalline S-(−)-amlodipine adipic acid salt anhydrous prepared in Example 1, the S-(−)-amlodipine besylate 2.5 hydrate prepared in Comparative Example 1, and the crystalline racemic amlodipine adipic acid salt anhydrous prepared in Comparative Example 2 were subjected to an acceleration test at 60° C.

<HPLC Analysis Condition>
Detector: UV absorbance (at 237 nm),
Column: Octadecyl silica gel C18 (4.6 mm×150 mm, 5□),
mobile phase: Potassium dihydrogen phosphate monobasic (0.03 M): Methanol=4:6 (by volume)
Flow rate: 1.5 ml/min.
The results are summarized in Table 3, below.

TABLE 3

| | Initial Stage | 1 Week | 2 Weeks | 4 Weeks |
|---|---|---|---|---|
| Ex. 1 | 99.8% | 99.8% | 99.7% | 99.7% |
| C. Ex. 1 | 99.6% | 99.6% | 99.5% | 99.5% |
| C. Ex. 2 | 99.8% | 99.8% | 99.7% | 99.7% |

(Unit: % HPLC)

All of the crystalline S-(−)-amlodipine adipic acid salt anhydrous of the present invention (Example 1), S-(−)-amlodipine besylate 2.5 hydrate (Comparative Example 1) and the crystalline racemic amlodipine adipic acid salt anhydrous (Comparative Example 2), as seen in Table 8, were found to undergo little change in content as measured by the 60° C. acceleration test, suggesting that the crystalline S-(−)-amlodipine adipic acid salt anhydrous of the present invention was as good in thermal stability as S-(−)-amlodipine besylate 2.5 hydrate.

2. Thermal Stability in Liquid State

To evaluate the thermal stability of samples in a liquid state, the crystalline S-(−)-amlodipine adipic acid salt anhydrous prepared in Example 1, the S-(−)-amlodipine besylate 2.5 hydrate prepared in Comparative Example 1, and the crystalline racemic amlodipine adipic acid salt anhydrous prepared in Comparative Example 2 were dissolved in distilled water before storage for 4 weeks at 25° C. in the dark with the content thereof monitored. The observation was made under the same conditions as in the HPLC analysis for evaluating the thermal stability of samples in a solid state.

This thermal stability test revealed that none of the crystalline S-(−)-amlodipine adipic acid salt anhydrous of the present invention (Example 1), S-(−)-amlodipine besylate 2.5 hydrate (Comparative Example 1) or the crystalline racemic amlodipine adipic acid salt anhydrous (Comparative Example 2) were degraded. Also, no significant content changes were observed in any of them.

EXPERIMENTAL EXAMPLE 4

Photostability Test

The crystalline S-(−)-amlodipine adipic acid salt anhydrous prepared in Example 1, the S-(−)-amlodipine besylate 2.5 hydrate prepared in Comparative Example 1, and the crystalline racemic amlodipine adipic acid salt anhydrous prepared in Comparative Example 2 were stored for 4 weeks at 25° C. in a photostable chamber in accordance with ICH guidelines and were exposed to a light source. An observation was made of content (HPLC) change under the same conditions as in the HPLC analysis for evaluating the thermal stability of samples.

The results are given in Table 4, below.

TABLE 4

| | Initial Stage Content(HPLC) | After 4 weeks at 25° C. Content(HPLC) |
|---|---|---|
| Ex. 1 | 99.5% | 93.9% |
| C. Ex. 1 | 99.2% | 79.6% |
| C. Ex. 2 | 99.5% | 99.1% |

As shown in Table 4, only a slight content change was observed in both the crystalline S-(−)-amlodipine adipic acid salt anhydrous (Example 1) of the present invention and the crystalline racemic amlodipine adipic acid salt anhydrous (Comparative Example 2). In contrast, S-(−)-amlodipine besylate 2.5 hydrate (Comparative Example 1) turned yellow from white with a decrease in content from 99.2% to 79.6% during exposure to the light source.

Thus, the crystalline S-(−)-amlodipine adipic acid salt anhydrous according to the present invention was confirmed to be highly photostable. Photostability is a very important factor for anti-hypertensives because they are generally administered over a long period of time.

INDUSTRIAL APPLICABILITY

The crystalline S-(−)-amlodipine adipic acid salt anhydrous produced by the method of the present invention exhibits excellent physical and chemical properties including non-hygroscopicity, solubility, thermal stability, and photostability, and is superior in formulation processability and long-term storage safety.

The invention claimed is:

1. Crystalline S-(−)-amlodipine adipic acid salt anhydrous, represented by the following Chemical Formula 1:

<Chemical Formula 1>

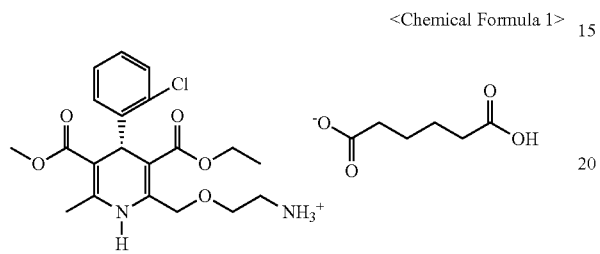

wherein the crystalline S-(−)-amlodipine adipic acid salt anhydrous has X-ray diffraction peaks at diffraction angles of 9.6°, 11.0°, 13.54°, 14.52°, 14.58°, 15.30°, 17.48°, 17.92°, 17.98°, 18.02°, 19.34°, 21.14°, 22.14°, 23.20°, 24.26°, 25.32°, 26.60°, 27.14°, 27.26°, 28.26°, 28.62°, 30.62°, 31.96°, 32.02°, 33.06°, 35.36°, 35.98°, 36.04°, 37.42°, and 44.68°, with a melting point ranging from 134 to 136° C.

2. A method for preparing Crystalline S-(−)-amlodipine adipic acid salt anhydrous represented by the following Chemical Formula 1, comprising a reaction between S-(−)-amlodipine and adipic acid in an inert solvent:

<Chemical Formula 1>

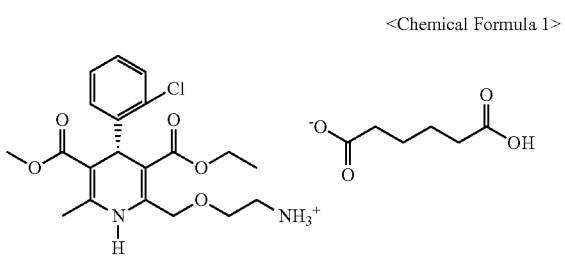

wherein the crystalline S-(−)-amlodipine adipic acid salt anhydrous has X-ray diffraction peaks at diffraction angles of 9.6°, 11.0°, 13.54°, 14.52°, 14.58°, 15.30°, 17.48°, 17.92°, 17.98°, 18.02°, 19.34°, 21.14°, 22.14°, 23.20°, 24.26°, 25.32°, 26.60°, 27.14°, 27.26°, 28.26°, 28.62°, 30.62°, 31.96°, 32.02°, 33.06°, 35.36°, 35.98°, 36.04°, 37.42°, and 44.68°, with a melting point ranging from 134 to 136° C.

3. The method according to claim 2, wherein the inert solvent is selected from a group consisting of ethyl acetate, ethanol, isopropanol, acetonitrile, hexane, isopropyl ether and a combination thereof.

4. The method according to claim 3, wherein the inert solvent is a combination of ethanol and isopropanol.

5. The method according to claim 2, wherein the adipic acid is used in an amount of 1~2 equivalents per equivalent of S-(−)-amlodipine.

6. A pharmaceutical composition for prevention or treatment of cardiovascular diseases, comprising the crystalline S-(−)-amlodipine adipic acid salt anhydrous of claim 1 as an active ingredient.

7. The pharmaceutical composition according to claim 6, wherein the pharmaceutical composition is in a dosage form of a tablet, a capsule, a granule, a pill or an injection.

* * * * *